United States Patent [19]
Arnold

[11] Patent Number: 5,970,718
[45] Date of Patent: Oct. 26, 1999

[54] PERSONAL HEAT CONTROL

[75] Inventor: Anthony P Arnold, London, United Kingdom

[73] Assignee: Kool Limited, Surrey, United Kingdom

[21] Appl. No.: 09/058,370

[22] Filed: Apr. 9, 1998

[51] Int. Cl.⁶ ............................... F25B 21/02; A61F 7/00
[52] U.S. Cl. ......................... 62/3.5; 62/259.3; 607/109
[58] Field of Search .................................. 62/3.5, 259.3, 62/3.2, 3.3; 2/458, DIG. 1, DIG. 11; 607/108, 109, 112, 99, 114, 104, 148

[56] References Cited

U.S. PATENT DOCUMENTS

| | | | |
|---|---|---|---|
| 2,798,494 | 7/1957 | Sukacev | 62/3.5 |
| 2,938,356 | 5/1960 | McMahon | 62/3.5 |
| 3,099,137 | 7/1963 | Jamison | 62/3.5 |
| 3,132,688 | 5/1964 | Nonak | 62/3.5 |
| 4,470,263 | 9/1984 | Lehovec et al. | 62/3.5 |
| 4,860,748 | 8/1989 | Chiurco et al. | 601/148 |
| 5,562,604 | 10/1996 | Yablon et al. | 601/148 |
| 5,800,490 | 9/1998 | Patz et al. | 607/108 |
| 5,802,865 | 9/1998 | Strauss | 62/259.3 |

*Primary Examiner*—William Doerrler
*Attorney, Agent, or Firm*—Welsh & Katz, Ltd.; Thomas W. Tolpin

[57] ABSTRACT

A personal heat control has a housing (4) accommodating a Peltier-effect unit (1), one or more batteries 15 and a timing switch (9) for selective energisation of the unit (1). The housing (4) is releasably attached to a part of a person's body, e.g. the wrist, by a strap (5) with a cooling surface cooled by the unit (1) in contact with the body part to enhance heat transfer between the person's body and the surrounding air for comfort and refreshment purposes when the unit (1) is energised.

19 Claims, 4 Drawing Sheets

FIGURE 1
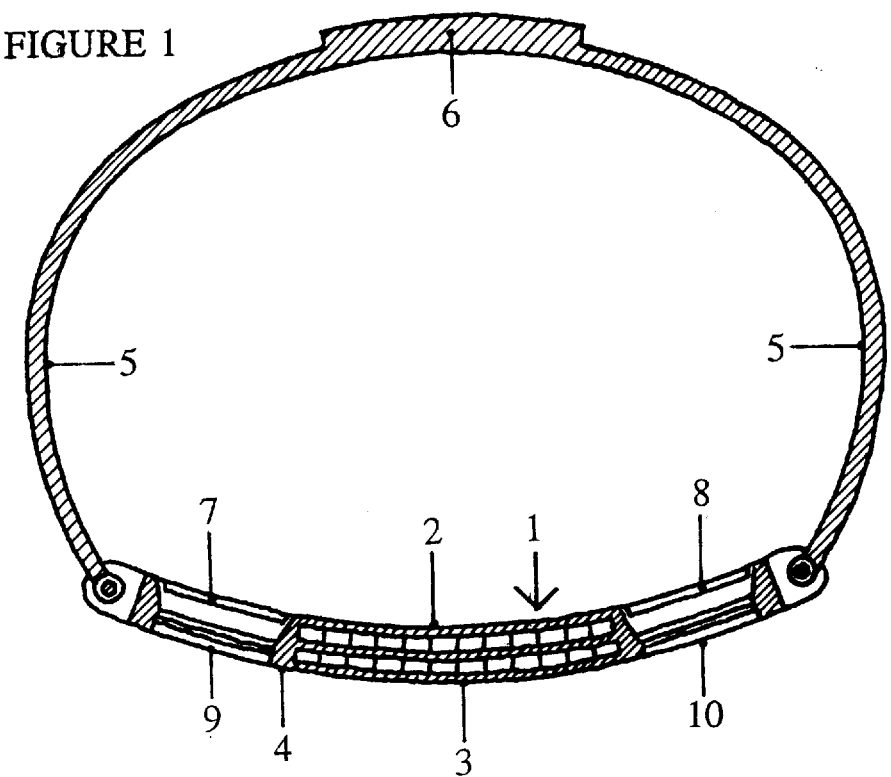
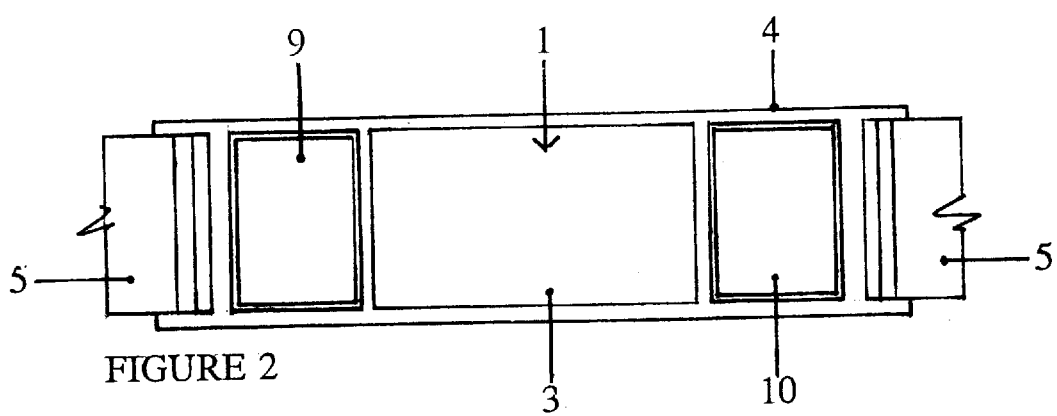
FIGURE 2
FIGURE 3
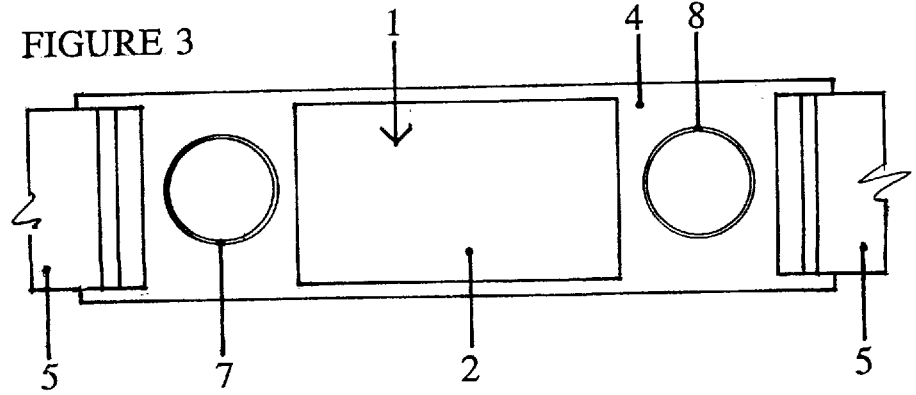

PERSONAL HEAT CONTROL

This invention relates to personal heat control, and in this respect is concerned especially with devices to be worn on the person for effecting cooling, or warming, of the body.

According to one aspect of the present invention there is provided a personal heat control device for a person's body, comprising a cooling surface and a heating surface thermally insulated from the cooling surface, a Peltier-effect unit for cooling the cooling surface and heating the heating surface, the Peltier-effect unit being accommodated in or on housing means connected to attachment means for attachment of the device to a part of the person's body with one of said surfaces in contact with the skin at said body part, and switch means for selective connection of the Peltier-effect unit to electrical-powering means for actuation of the Peltier-effect unit, the housing means being arranged to accommodate the switch means and the electrical-powering means whereby the device is a self-contained portable heat control device.

The device enables heat transfer to be made from or to the body for comfort or refreshment purposes, and in this respect the device may be adapted to be worn on the body, for example in the nature of a wrist- or head-band, with the heating surface or the cooling surface held, for example, against the inside of the wrist or against the forehead, where blood vessels are close to the skin surface. In this way rapid and effective transfer of heat for cooling or warming the body can be achieved. More particularly, the cooling or warming can be achieved with economical expenditure of electrical energy and under close control.

In the latter respect, the electrical-powering means may involve one or more batteries, for example re-chargeable lithium ion batteries or primary thin cell batteries, one or more solar panels, or an electrical generator (for example driven by a clockwork motor, or by kinetic energy using a motion-sensitive mechanism) that is carried by the housing means for providing current to energise the Peltier-effect unit. Conveniently the Peltier-effect unit, the switch means and the electrical-powering means are accommodated in a single housing, although the electrical-powering means and may be the switch means could be disposed in a separate housing to that of the Peltier effect unit. The switch means may be, for example, a toggle or other mechanical switch that is operated manually for on-off control of current flow, but may involve an electronic timing or pulsing circuit to regulate the flow.

Personal heat-control devices in accordance with the present invention, will now be described, by way of example, with reference to the accompanying drawings, in which:

FIG. 1 shows a device according to the invention in side elevation;

FIGS. 2 and 3 are plan views of the device of FIG. 1 from opposite sides, with an attachment strap of the device broken away;

Figure 4:
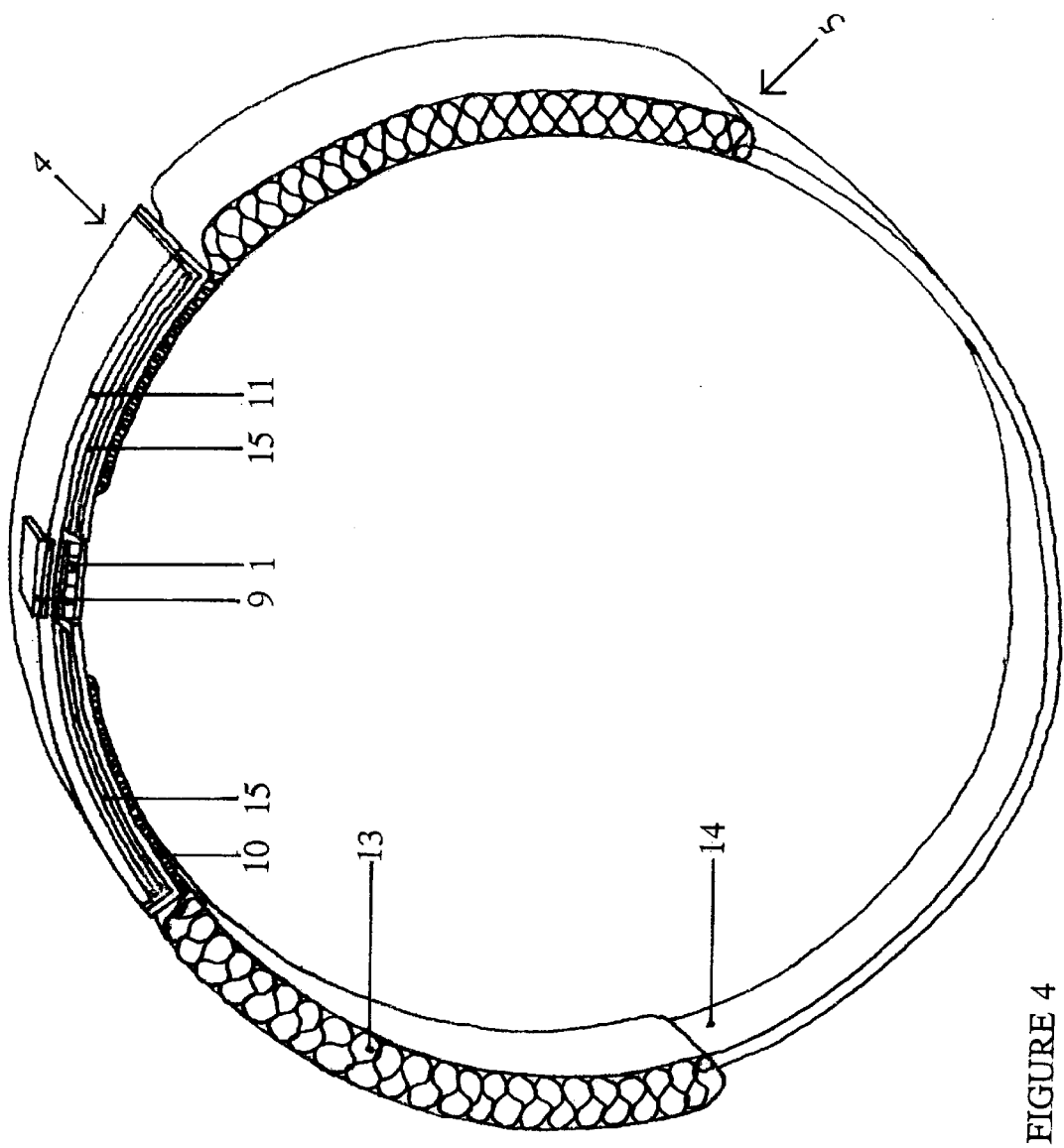
FIG. 4 shows an illustrative sectional view of a preferred embodiment of a personal heat-control device for use as a headband, viewed from the right and above.

Referring to FIGS. 1 to 3, a heat-control device, for use in cooling the body and adapted to be worn on the wrist, includes a Peltier-effect or thermoelectric-cooling unit 1 having ceramic heat-conductive cooling and heating surfaces, 2 and 3 respectively, on opposite sides. The unit 1 is set within a stainless-steel or other elongate housing 4 that is carried by a leather, metal or fabric strap 5 for attaching the device around the wrist. The strap 5 includes in the latter respect a buckle 6 for fastening the housing 4 tightly to the wrist with the surface 2 inside and located against the skin on the inside of the wrist. The housing 4 is bowed outwardly slightly so as to conform to the wrist and ensure good heat conduction between the surface 2 and the blood vessels just beneath the skin.

Two compartments 7 and 8 for electric primary-cell or rechargeable batteries (not shown) are provided on the inside of the housing 4, the batteries being connected within the housing 4 to energise the Peltier-effect unit 1 via a toggle on-off switch 9 that is mounted on the outside of the housing 4. Energisation of the unit 1 causes heat to be absorbed by the inside surface 2 and given off by the outside surface 3. The heat absorbed by the surface 2 in contact with the inside of the wrist cools the body, and the heat given out by the surface 3 is dissipated into the atmosphere.

The wearer of the device operates the switch 9 to energise the unit 1 for a short while whenever the benefit of personal cooling is required. The period of time for which it remains energised may be at his/her choice, but such choice will normally take account of the desirability to conserve battery-power. A digital indicator 10, mounted on the outside of the housing 4, gives an indication of battery performance/life to assist in this regard.

Although the device of FIGS. 1 to 3 has been described above as including the strap 5 fastened by a buckle, other means of fastening may be use; for example, a partial-release tensioner as used with metal watch straps may be used, or, especially where the strap is fabric, the fastening may be by means of fabric hook-and-loop engagement such as involved in fastenings sold under the Registered Trade Mark VELCRO. Alternatively, the strap 5 may simply be an elastic loop. Moreover, a watch (or other item of personal wear) may be incorporated in the device, this being located, for example, in place of the buckle 6 as illustrated in FIG. 1.

The device described with reference to FIGS. 1 to 3 may be worn as an anklet, or when provided with a larger strap, elsewhere on the leg, or may be worn on the foot (perhaps within a shoe). Furthermore, when provided, for example, with an elastic strap that incorporates towelling, it may be worn as a head-band as described below. The degree of bowing of the housing of the device is arranged to conform to, or may be made to be adaptable to, what is appropriate for the location on the body where the device is to be worn.

Figure 5:
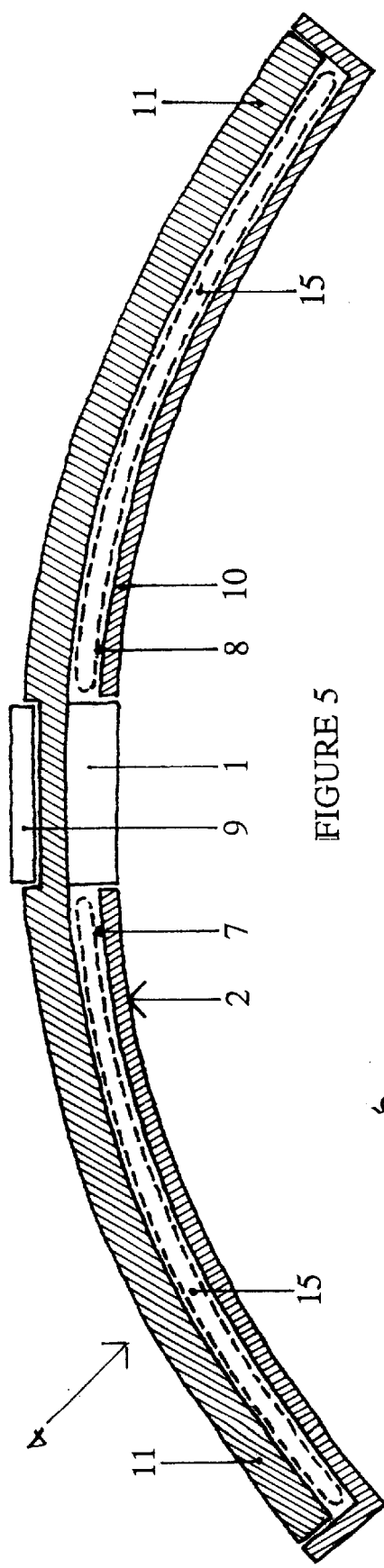
FIG. 5 shows a cross-section through the housing of the device illustrated in FIG. 4.
Figure 6:
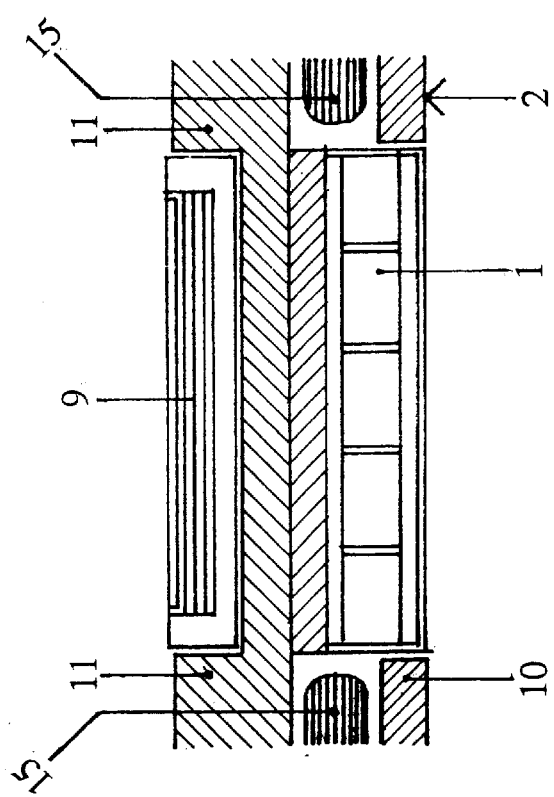
FIG. 6 is an enlarged cross-section of the centre of the housing shown in FIG. 5.

Referring to FIGS. 4 to 6, in a preferred embodiment of the device the thermoelectric-cooling unit 1 is disposed within a central opening in a metal, e.g. aluminium or stainless steel, lower casing 10 of the subarcuate elongate housing 4, and the underside of the unit 1 lies flush with the inside surface 2 of the housing. The lower casing has side walls bordering an outwardly open channel or trough for receipt of a good heat conductive material, e.g. aluminium or copper, upper casing member 11 having a circumjacent layer of insulating material to thermally isolate the casings 10,11 from each other. The upper casing member 11 is affixed flush with the upper surfaces of the lower casing side walls, such as by suitable fasteners, e.g. countersunk screws. (Alternatively, the lower casing member may be fitted within a side wall carried by the upper casing member.) Two lithium-ion rechargeable batteries with solid state electrolyte or lithium thin cell primary batteries 15 are housed on either side of the unit 1 within compartments 7,8 defined by casings 10,11 and the batteries 15 are electrically connected, e.g. by wires or conductive strips, to energise the unit 1 on activation by the wearer of the device of a solid state electronic timing switch 9 mounted on the outside of the casing 11. It has been found that a pleasant cooling effect is achieved when the unit is energised for not more than 1 minute, e.g. about 30 seconds or less, and preferably around 15 seconds. Reactivation of the unit may be prevented for a short period, not less than the energisation time, immediately after the operation of the device, by the timing switch circuitry to allow heat generated in the unit to disperse through the outer casing 11, which serves as a heat sink. The surface area of the heat sink may be several times the size of the cooling surface, e.g. five times larger, to promote rapid heat dissipation. The cooling unit 1 is fixed within the housing 4 and to the inside of the upper casing 11 by suitable adhesive 12.

Adjacent the cooling unit on the inside surface 2 of the housing are cooperating fabric hoop-and-loop fasteners, e.g. fasteners sold under the Registered Trade Mark VELCRO, to releasably secure the housing to towelling portions 13 of a strap 5 for retaining the housing on the wearers' temple, the towelling portions 13 being joined at their bases by an elastic strip 14. Of course, an appropriately scaled down version of the device depicted in FIGS. 4 to 6 could be fitted onto a person' wrist or ankle.

Figure 7:
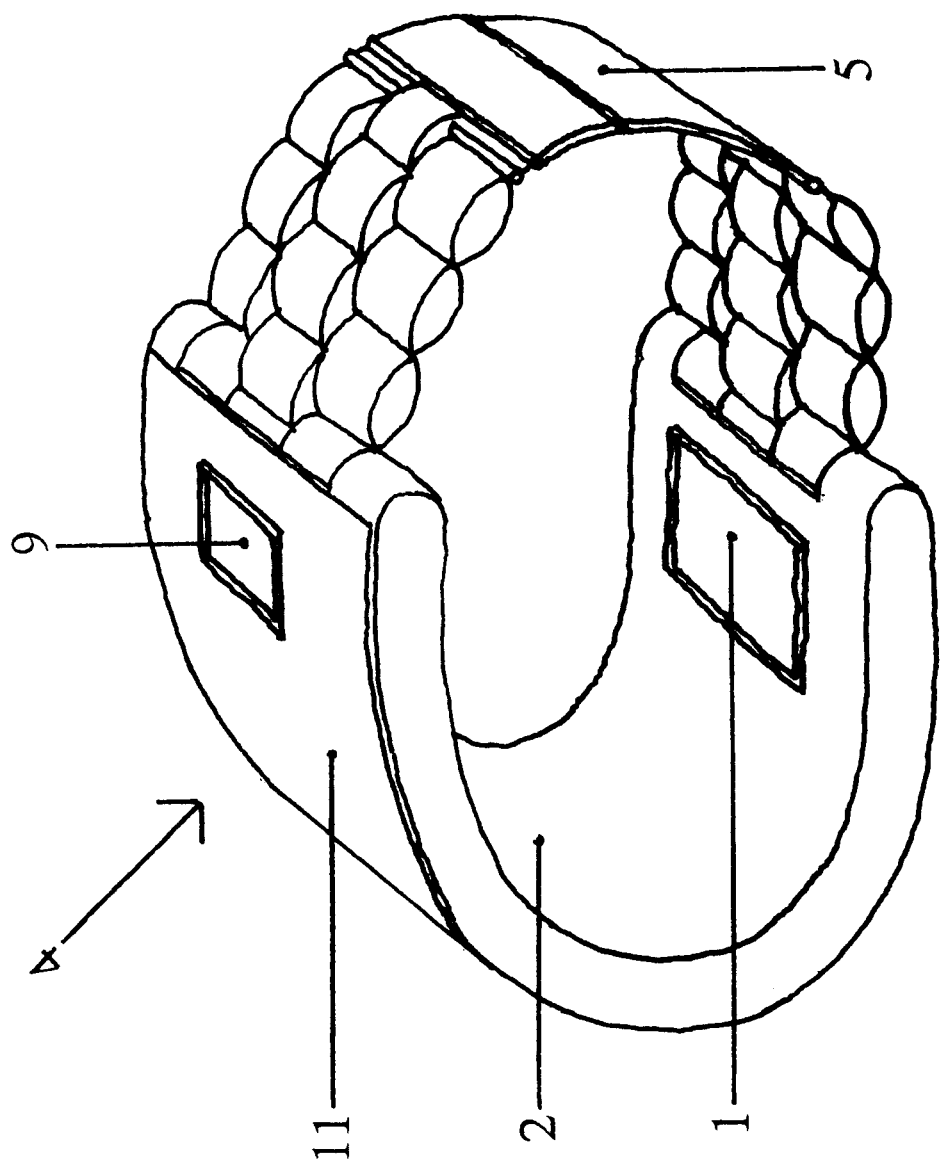
FIG. 7 is an illustration of an alternative configuration of the preferred embodiment and to be used as a wrist band.

FIG. 7 shows an alternative configuration of the preferred embodiment of the device having a generally C-shaped or semi-circular housing shaped to fit the wrist and containing a single lithiun-ion rechargeable battery with solid state electrolyte or a lithium thin cell primary battery. The timing switch 9 and unit 1 are situated at opposed ends and on opposite sides of the housing with the device located to the side of the wrist and the switch 9 preferably disposed upwardly of the wrist to facilitate its activation. The device is shown in FIG. 7 with a strap 5 made from stainless steel with a clasp or buckle to hold it firmly in place on the wearer's wrist, but it could equally be provided with a towelling and/or elastic strap as previously described. A highly thermally conductive strip or sheet of material, e.g. aluminium or stainless steel foil, can be spring mounted adjacent the cooling surface 2 to press against the skin and thereby ensure a good contact is achieved between the skin of the wearer and the unit. Additionally the sheet of material may have a larger surface area than the cooling surface of the unit to increase the cooling area of the unit.

The cooling effect of the device has been found to be most effective when the unit is positioned adjacent the blood vessels in the middle of the underside of the wearer's wrist or at the temple, as these blood vessels are close to the skin in this region and the blood cooled by the unit 1 is carried to other parts of the wearer's body. By concentrating the cooling effect of the device in this region of the wrist the size of the unit 1 can be minrimised without reducing its efficiency, and the number of times the batteries 15 can be energised before they require recharging or replacement can be maximised.

The utilisation of lithium-ion batteries with solid state electrolyte is advantageous as the batteries weigh less than known rechargeable batteries, e.g. nickel-cadmium batteries, of comparable power output and the batteries 15 can be molded to fit within the arcuate housing. Equally advantageously, lithium thin cell primary batteries could be used.

As well as being of advantage for comfort and refreshment during general, everyday activities, the device may find specific applications in the medical, surgical and sports contexts.

It will be appreciated that the device may be used to provide warming of the body by reversing the mounting of the unit 1 within the housing 4 so that the surface 3 contacts the skin. Alternatively, current flow to the unit may be reversed to achieve the same effect. Whether the device is used for heating or cooling, it is important to ensure that the temperature of the surface in contact with the skin remains within reasonable limits to avoid the possibility of injury to the wearer.

I claim:

1. A personal heat control device of a person's body, comprising, a cooling surface and a heating surface thermally insulated from the cooling surface, a Peltier-effect unit for cooling the cooling surface and heating the heating surface, the Peltier-effect unit being accommodated in or on housing means connected to attachment means for attachment of the device to a part of the person's body with one of said surfaces in contact with the skin at said body part, and switch means for selective connection of the Peltier-effect unit to electrical-powering means for actuation of the Peltier-effect unit, the housing means comprising a single housing being arranged to accommodate the switch means, the Peltier-effect unit and the electrical-powering means whereby the device is a self-contained portable heat control device, and the switch means comprises a timing switch to energise the unit for a set period of time when actuated.

2. A personal heat control device for a person's body, comprising a cooling surface and a heating surface thermally insulated from the cooling surface, a Peiltier-effect unit for cooling the cooling surface and heating the heating surface, a Peiltier-effect unit being accommodated in or on housing means connected to attachment means for attachment of the device to a part of the person's body with one of said surfaces in contact with the skin at said body part, and switch means for selective connection of the Peiltier-effect unit to electrical-powering means for actuation of the Peiltier-effect unit, the housing means comprising a single housing being arranged to accommodate the switch means, the Peltier-effect unit and the electrical-powering means whereby the device is self-contained portable heat control device, and the switch means comprises a timing switch to energise the unit for not more than one minute when actuated.

3. A personal heat control device for a person's body, comprising a cooling surface and a heating surface thermally insulated from the cooling surface, a Peltier-effect unit for cooling the cooling surface and heating the heating surface, the Peltier-effect unit being accommodated in or on housing means connected to attachment for attachment of the device to a part of the person's body with one of said surfaces in contact with the skin at said body part, and switch means for selective connection of the Peltier-effect unit to electrical-powering means for actuation of the Peltier-effect unit, the housing means comprising a single housing being arranged to accommodate the switch means, the Peltier-effect unit and the electrical-powering means whereby the device is a self-contained portable heat control device, the switch means comprises a timing switch to energise the unit for a set period of time when actuated, and said switch preventing reactivation of the unit for a period of time.

4. A personal heat control device according to claim 1 wherein the cooling surface is arranged to contact with the body part.

5. A personal heat control device for a person's body, comprising a cooling surface and a heating surface thermally insulated from the cooling surface, a Peltier-effect unit for cooling the cooling surface and heating the heating surface, the Peltier-effect unit being accommodated in or on housing means connected to attachment means for attachment of the device to a part of the person's body with one of said surfaces in contact with the skin at said body part, and switch means for selective connection of the Peltier-effect unit to electrical-powering means for actuation of the Peltier-effect unit, the housing means being- arranged to accommodate the switch means and the electrical-powering means whereby the device is a self-contained portable heat control device;

wherein the Peltier-effect unit, the switch means and the electrical-powering means are accommodated in a single housing;

wherein the switch means comprises a timing switch to energise the unit for a set period of time when actuated;

wherein the timings switch energises the unit for more than one minute; and wherein the timing switch prevents the reactivation of the unit for a period of time not less than the energisation time.

6. A personal heat control device according to claim 3 wherein the electrical powering means comprises one or more batteries.

7. A personal heat control device according to claim 6, wherein the or each battery is a lithium-ion rechargeable battery or a lithium thin cell primary battery.

8. A personal heat control device according to claim 3 wherein the electrical powering means comprise more solar panels.

9. A personal heat control device according to claims 3 wherein the cooling surface is arranged for contact with the body part.

10. A personal heat control device according to claim 9, wherein the cooling surface is defined by a layer of highly thermally conductive material disposed interjacent the Peltier-effect unit and the body part when the device is worn.

11. A personal heat control device according to the claim 3 wherein the housing is substantially rigid and arcuate to conform to the body part to which the device is fitted.

12. A personal heat control device according to claim 3 wherein the attachment means comprises a strap which is elastic or can be tightened to hold the cooling surface in close contact with the skin of the body part.

13. A personal heat control device for a person's body, comprising a cooling surface and a heating surface thermally insulated from the cooling surface, a Peltier-effect unit for cooling the cooling surface and heating the heating surface, the Peltier-effect unit being accommodated in or on housing means connected to attachment means for attachment of the device to a part of the person's body with one of said surfaces in contact with the skin at said body part, and switch means for selective connection of the Peltier-effect unit to electrical-powering means for actuation of the Peltier-effect unit, the housing means being arranged to accommodate the switch means and the electrical-powering means whereby the device is a self-contained portable heat control device;

wherein the Peltier-effect unit, the switch means and the electrical-powering means are accommodated in a single housing;

wherein the switch means comprises a timing switch to energise the unit for a set period of time when actuated;

wherein the timing switch energises the unit for more than one minute, and wherein the timing switch prevents reactivation of the unit for a period of time not less than the energization time.

14. A personal heat control device according to claim 1 wherein the electrical powering means comprise one or more solar panels.

15. A personal heat control device according to claim 1 wherein the cooling surface is arranged of contact with the body part.

16. A personal heat control device according to claim 2 wherein the housing is substantially rigid and arcuate to conform to the body part to which the device is fitted.

17. A personal heat control device according to claim 2 wherein the housing is substantially rigid and arcuate to conform to the body part to which the device is fitted.

18. A personal heat control according to claim 3 wherein the timing switch prevents the reactivation of the unit for a period of not less than the energisation time.

19. A personal heat control device according to claim 2 wherein the electrical powering means comprise one or more solar panels.

* * * * *